(12) United States Patent
    Quiray

(10) Patent No.: US 8,598,403 B2
(45) Date of Patent: Dec. 3, 2013

(54) INFANT NASAL SEPTUM PROTECTIVE DEVICE

(75) Inventor: Leah A. Quiray, Staten Island, NY (US)

(73) Assignee: LQ Product & Devices, LLC, Staten Island, NY (US)

( * ) Notice: Subject to any disclaimer, the term of this patent is extended or adjusted under 35 U.S.C. 154(b) by 248 days.

(21) Appl. No.: 13/117,203

(22) Filed: May 27, 2011

(65) Prior Publication Data
US 2012/0037167 A1 Feb. 16, 2012

Related U.S. Application Data

(60) Provisional application No. 61/372,328, filed on Aug. 10, 2010.

(51) Int. Cl.
*A61F 13/00* (2006.01)
*A61M 16/00* (2006.01)

(52) U.S. Cl.
USPC ........................................ 602/41; 128/207.17

(58) Field of Classification Search
USPC ............. 128/200.24, 207.18, 204.18, 205.25; 602/1, 5, 41–57; 604/304–308, 19, 48, 604/93.01, 174, 180
See application file for complete search history.

(56) References Cited

U.S. PATENT DOCUMENTS

| | | | | |
|---|---|---|---|---|
| 3,677,250 A | * | 7/1972 | Thomas | 604/180 |
| 4,114,626 A | * | 9/1978 | Beran | 604/180 |
| 4,534,342 A | * | 8/1985 | Pexa | 602/74 |
| 4,823,789 A | * | 4/1989 | Beisang, III | 128/207.18 |
| 5,735,272 A | * | 4/1998 | Dillon et al. | 128/207.18 |
| 5,769,089 A | * | 6/1998 | Hand et al. | 128/858 |
| 5,817,039 A | * | 10/1998 | Raunig | 602/5 |
| 5,833,663 A | * | 11/1998 | Bierman et al. | 604/174 |
| 2003/0236480 A1 | * | 12/2003 | Landis | 602/54 |
| 2005/0113190 A1 | * | 5/2005 | Gagnon | 473/422 |
| 2010/0000534 A1 | * | 1/2010 | Kooij et al. | 128/204.18 |

* cited by examiner

*Primary Examiner* — Patricia Bianco
*Assistant Examiner* — Tarla Patel
(74) *Attorney, Agent, or Firm* — Kane Kessler, P.C.; Paul E. Szaho

(57) ABSTRACT

An infant nasal septum protective device has an H-shaped configuration including a first portion that adheres to the outside of the nose when in use, a second portion that adheres to the upper lip when in use, and a third portion that extends between and interconnects the first and second portions in a position overlying the septum when in use, to help protect the septum.

10 Claims, 3 Drawing Sheets

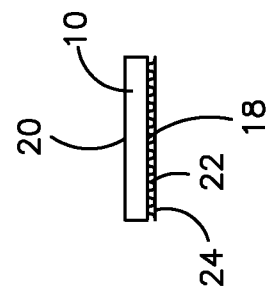
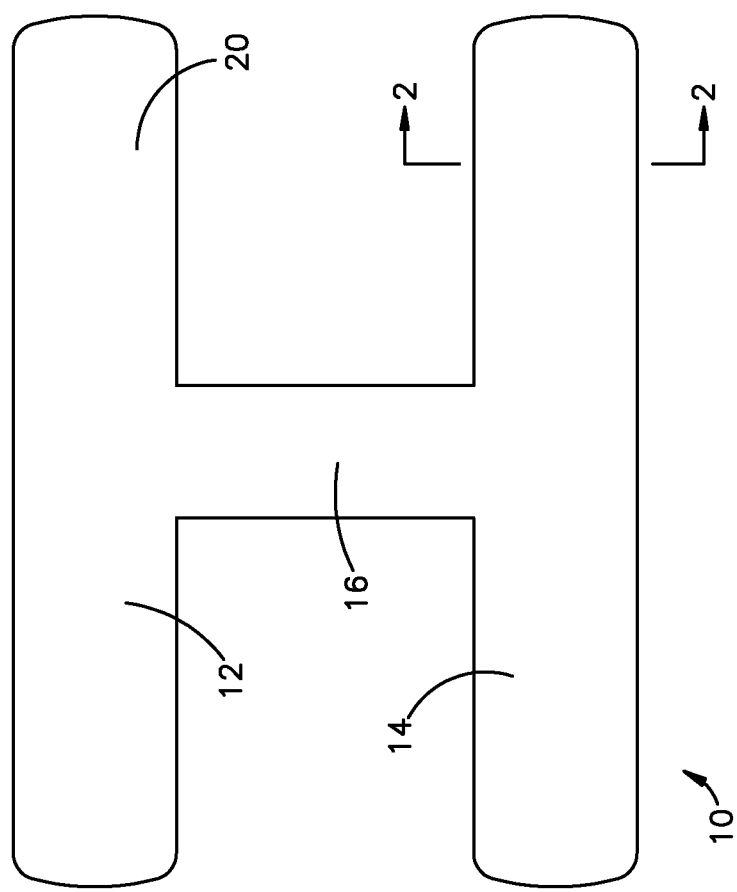

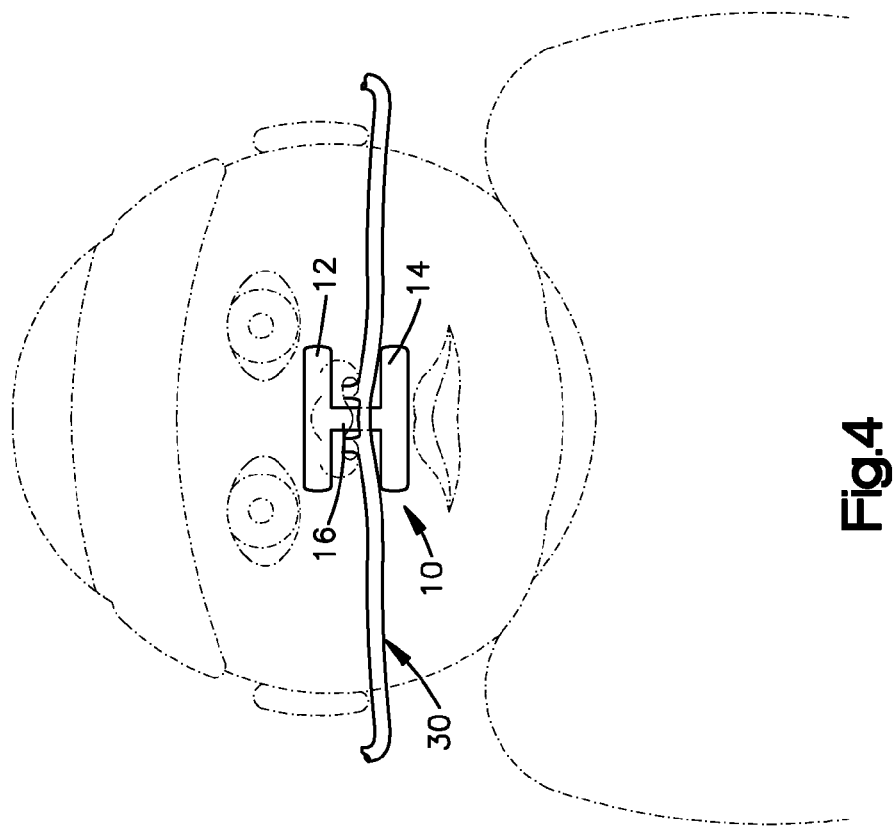
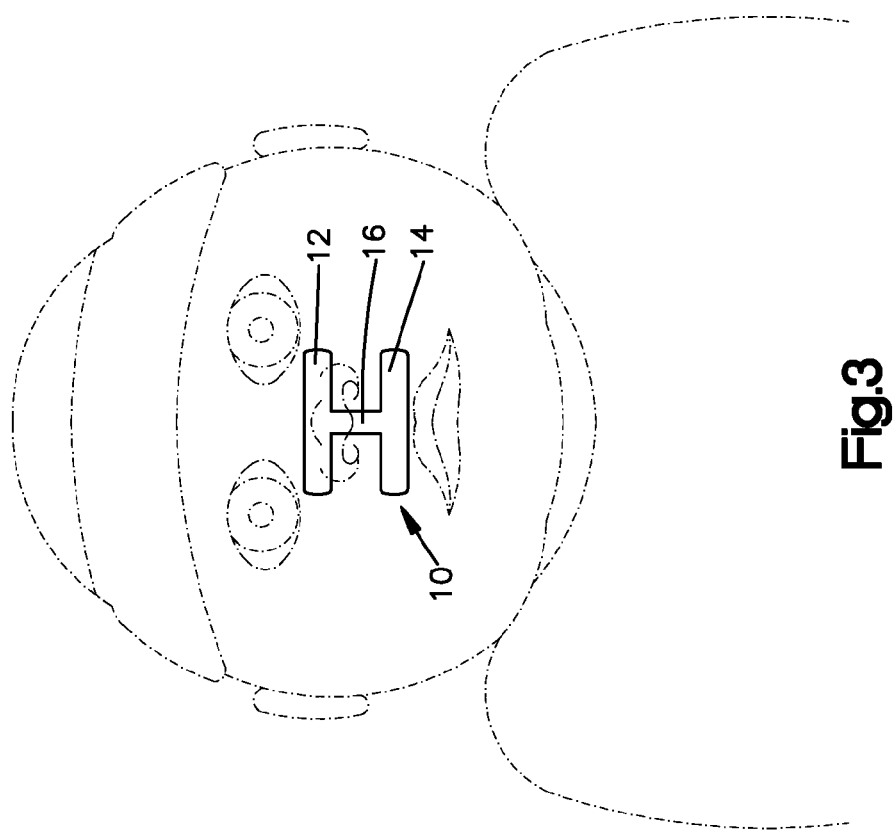

INFANT NASAL SEPTUM PROTECTIVE DEVICE

RELATED APPLICATIONS

This application claims the benefit of U.S. Provisional Patent Application No. 61/372,328, filed Aug. 10, 2010, the entire disclosure of which is incorporated by reference.

BACKGROUND OF THE INVENTION

This invention relates to an infant nasal septum protective device. The nasal septum is the portion of a human's nose that separates the left and right nostrils of the nose. In an infant, especially a premature infant, the septum is fragile. Many premature infants need oxygen therapy, which involves the use of a nasal cannula or a nasal CPAP device. Such devices can rub on or wear on the septum, thereby damaging the septum. Also, the skin of the septum becomes dry and cracks because of the oxygen application. In some cases, especially with prolonged nasal therapy, the septum can be severely damaged or even destroyed. It is desirable to prevent this from happening.

BRIEF DESCRIPTION OF THE DRAWINGS

Features of the invention will become apparent to one of ordinary skill in the art to which the invention pertains, from a reading of the following specification together with the accompanying drawings, in which:

FIG. 1 is a view of a protective device that is a first embodiment of the invention, showing the H-shaped configuration of the device;

FIG. 2 is a sectional view taken along the line 2-2 of FIG. 1;

FIG. 3 illustrates the device of FIG. 1 applied to an infant's nasal area;

FIG. 4 illustrates the device of FIG. 1 in use with a nasal cannula;

DETAILED DESCRIPTION

Figure 6:
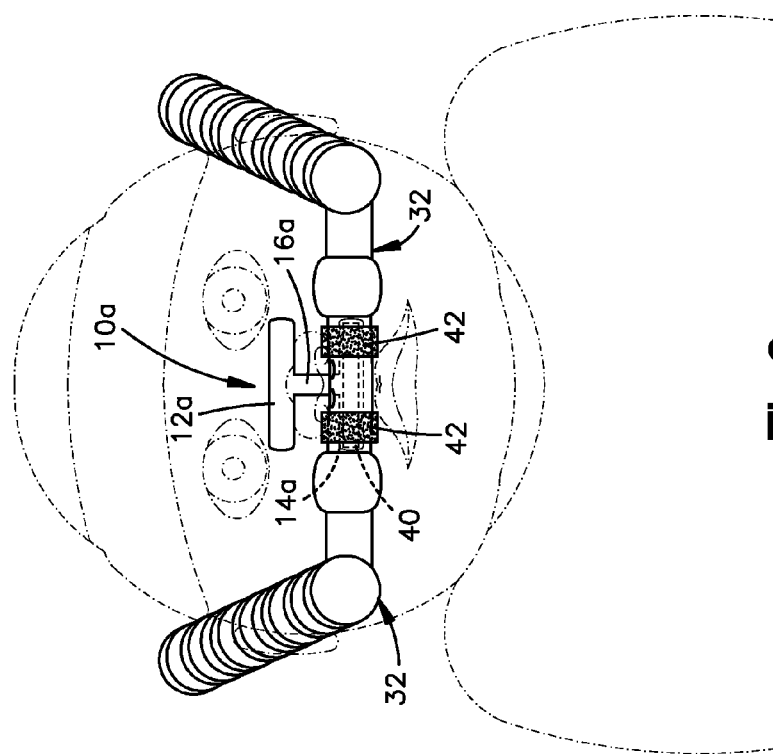
FIG. 6 illustrates the device of FIG. 5 in use with a nasal CPAP device.

This invention relates to an infant nasal septum protective device. The invention is applicable to devices of varying and different constructions. As representative of the invention, FIG. 1 illustrates a device 10 that is a first embodiment of the invention.

The device 10 is adapted to be secured to an infant's face and to protect the infant's nasal septum when oxygen therapy is being administered.

The device 10 is generally H-shaped as viewed in FIG. 1. The H-shaped configuration includes an upper portion or nose portion 12 (nose bridge strip) that is adapted to overlie the nose bridge area extending from left to right. The device 10 also includes a lower portion or lip portion 14 (upper lip strip) adapted to overlie and extend along the infant's upper lip in a direction generally laterally and parallel to the upper portion. The device 10 also includes a middle portion or septum protector strip 16 that extends perpendicularly between the upper portion 12 and the lower portion 14.

The device 10 is made of a sheet material that is flexible and that is substantially planar. The device 10 is preferably made from a hydrocolloid adhesive material of the type that is widely used in hospitals for dressings and bandages and that was developed to protect a wound from contamination. This material provides a moist wound-healing environment, thus providing both medical benefit and comfort to the patient.

The material of the device 10 has an inner major side surface 18 (FIG. 2) that is presented toward the patient's skin when the device is in use, and an opposite outer major side surface 20. An adhesive 22 is provided on the inner major side surface 18 of the device 10. Specifically, in the preferred embodiment, the entire back surface 18 of the device 10 is adhesive in order that every portion of the device may be secured to the skin, in a stabilized position. Thus, no separate taping is needed. A release strip or glue strip 24, such as is found on a common bandage, may cover the adhesive material 22 until the device 10 is ready for use.

The material from which the device 10 is made has a balanced texture appropriate to ensure secure application of the device to the skin and deliver effectiveness of the product. Thus, the device 10 not only blocks contact of the oxygen device with the skink but also lessens the pressure exerted on the septum. The material is flexible like a bandage or dressing to conform to the infant's facial configuration. The adhesiveness of the material allows the stable fixation of the device 10 to the skin. Other suitable materials can be used.

In use, the device 10 is attached completely to the nasal area and septum of the patient without the use of any other component, only the material itself. To install or place the device 10 on the infant, the caregiver should first ensure that both hands are clean by washing the hands thoroughly, then choose the appropriate size device according to the patient's weight and gestational age.

The device 10 may be provided in several different sizes to fit infants of different sizes and gestational ages. Extra small may be suitable for an infant who is under one kilogram and under 27 weeks of gestational age. Small may be suitable for an infant who is under 1.5 kilograms and 28-31 weeks of gestational age.

Medium may be suitable for an infant who is 1.5 to 2.5 kilograms and 32-36 weeks of gestational age. Large may be suitable for an infant who is over 2.5 kilograms and over 36 weeks of gestational age. One suitable size range is upper and lower portions being from 0.5 cm to 0.75 cm in width and 5.0 cm to 7.0 cm in length, with the intermediate septum portion being 0.5 cm or more in width and 1.0 cm to 2.0 cm in length.

Once the right size is chosen, the device 10 is removed from its packaging. The portion of the glue strip 24 that is on the lip portion 14 is peeled off, and the exposed adhesive 22 on the lip portion of the device 10 is then applied to the infant's upper lip area, as shown in FIG. 3. More of the glue strip is 24 peeled off and the middle portion 16 of the device 10 is applied to the septum. Then the remainder of the glue strip 24 is removed from the upper portion 12, and the upper portion is applied across the nose, anchoring both ends on the infant's cheeks.

At this point, then, the device 10 is securely in place, and the appropriate oxygen supply device can be placed on the infant. If the oxygen supply device is a nasal cannula 30 as shown in FIG. 4, the two nasal extensions of the cannula fit into the infant's nostrils. The central portion 16 of the septum protector device 10 is disposed between the cannula 30 and the infant's septum. Thus, the central portion 16 of the device 10 prevents contact of the nasal cannula with the infant's septum, and helps to protect the septum. In addition, the moist wound-healing environment that is provided by the hydrocolloidal material of the device 10 helps to prevent drying and cracking of the skin of the septum.

Figure 5:
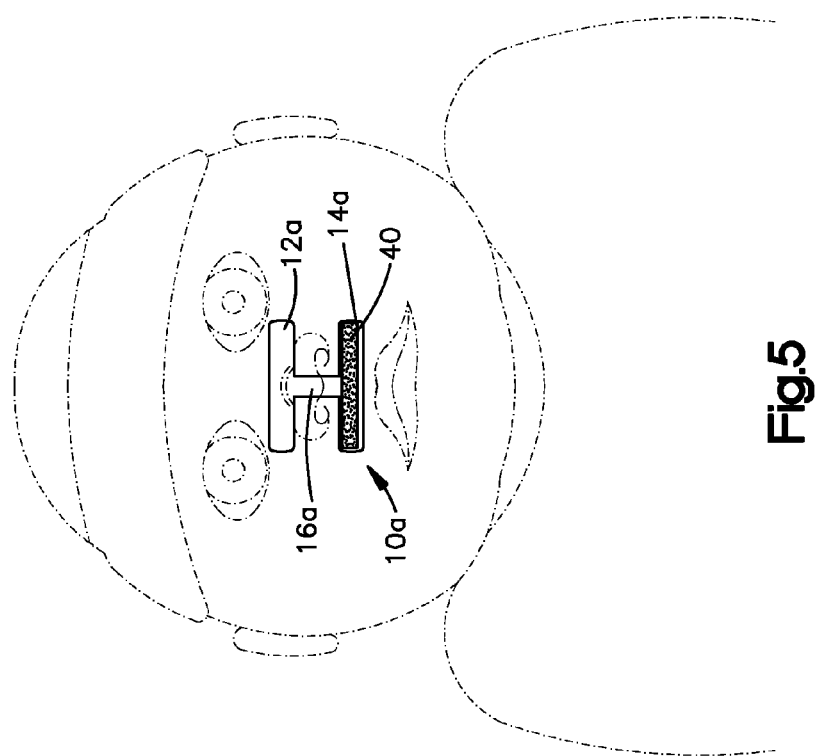
FIG. 5 is a view of similar to FIG. 1 of a protective device that is a second embodiment of the invention.

FIGS. 5 and 6 illustrate a device 10a that is a second embodiment of the invention. The device 10a is suitable for use with a nasal CPAP device 32 as shown in FIG. 6.

The device 10a is generally similar in construction to the device 10 but has an added Velcro hook strip 40 on the outside of the upper lip portion 14a of the device 10a. The Velcro hook strip 40 can be provided already affixed to the upper lip portion 14a of the device 10a. Alternatively, the Velcro hook strip 40 can be provided separately to be used with a device 10, in which case there would be provided an adhesive, for example on the back of the hook strip, to secure it on the device 10.

The device 10a also includes two separate Velcro loop strips 42 that are adapted to be manually wrapped around and thus secured to the tubing of the CPAP device 32. The Velcro loop strips 42 on the device 32 are then engageable with the Velcro hook strip 40 on the upper lip portion 14a of the device 10a, to secure the CPAP device onto the device 10a. Thus the device 10a helps to support the CPAP device 32 in the proper position on the infant's face, while at the same time the central portion 16a of the device 10a prevents contact of the CPAP device with the infant's septum and thus helps to protect the septum.

When the device 10 or 10a is in use, the caregiver should implement regular routine checks of the patients' nasal area, ensuring that the device remains properly and securely placed. The device's recommended usage period is 48 hours. The device should be removed from the patient once that usage period has elapsed. To remove the device, the caregiver can first prepare wet gauze or cotton balls. The entire area covered by the device is then carefully moistened, starting from the upper portion towards the septum area and to the lower portion. Then, the device is carefully peeled off, starting from the upper portion towards the septum area and to the lower portion.

The invention claimed is:

1. A protective device for use in protecting an infant's nasal septum when an oxygen supply device is being used on the infant, comprising:
    a first portion that adheres to the outside of the infant's nose when in use;
    a second portion that adheres to the infant's upper lip when in use; and
    a third portion that extends between and interconnects the first and second portions in a position overlying the infant's septum when in use;
    wherein the first portion is in the range of from 0.5 cm to 0.75 cm in width and in the range of from 5.0 cm to 7.0 cm in length;
    wherein the second portion is in the range of from 0.5 cm to 0.75 cm in width and in the range of from 5.0 cm to 7.0 cm in length; and
    wherein the third portion is in the range of 0.5 cm in width and from 1.0 cm to 2.0 cm in length.

2. A protective device as set forth in claim 1 that is made of a hydrocolloidal material with an adhesive inner side surface for adhering to the skin of an infant.

3. A protective device as set forth in claim 1 having an H-shaped configuration with the first portion and the second portion extending generally parallel to each other and the third portion extending generally perpendicular to and between the first portion and the second portion.

4. A protective device as set forth in claim 1 including a first fastener portion on the outer side surface of the second portion of the device, and a second fastener portion for placement on the oxygen supply device and engageable with the first fastener portion thereby to support the oxygen supply device on the second portion of the device and thus on the infant without direct contact with the infant's septum.

5. A protective device as set forth in claim 4 wherein the first and second fastener portions are hook and loop fastener portions.

6. A protective device for use with an oxygen supply cannula on an infant who has a nose with two nostrils separated by a nasal septum, the nose being disposed above the upper lip of the infant and between the two cheeks of the infant;
    the cannula including two nasal extensions that are sized to fit into the nostrils of the infant and also including an intermediate portion extending between the nasal extensions and thus extending laterally across the infant's nasal septum when the cannula is in place on the infant's nose;
    the protective device being used for protecting the infant's nasal septum when the cannula is in place on the infant's nose, the protective device comprising:
    a flexible sheet material having an outer major side surface and an inner major side surface, and an adhesive layer on the inner major side surface;
    the sheet material having an H-shaped configuration including:
    a first portion that adheres to the outside of the infant's nose when in use, extending laterally between the infant's cheeks, the height of the first portion being selected to fit onto the infant's nose bridge area above the nostrils and below the infant's eyes;
    a second portion that adheres to the infant's upper lip when in use, extending laterally between the infant's cheeks, the height of the second portion being selected to fit onto the infant's upper lip below the infant's nose and substantially completely above the infant's mouth; and
    a septum protector strip that extends transverse to the first and second portions and that interconnects the first and second portions and that overlies the infant's nasal septum when the protective device is in place on the infant's nose thereby to minimize contact between the intermediate portion of the cannula and the infant's nasal septum when the cannula is in place on the infant's nose.

7. A protective device as set forth in claim 6 that is made of a hydrocolloidal material with an adhesive inner side surface for adhering to the skin of an infant.

8. A protective device as set forth in claim 6 including a first fastener portion on the outer side surface of the second portion of the device, and a second fastener portion for placement on the oxygen supply device and engageable with the first fastener portion thereby to support the oxygen supply device on the second portion of the device and thus on the infant without direct contact with the infant's septum.

9. A protective device as set forth in claim 8 wherein the first and second fastener portions are hook and loop fastener portions.

10. A protective device as set forth in claim 6 wherein the first portion is in the range of from 0.5 cm to 0.75 cm in width and in the range of from 5.0 cm to 7.0 cm in length;
    wherein the second portion is in the range of from 0.5 cm to 0.75 cm in width and in the range of from 5.0 cm to 7.0 cm in length; and
    wherein the third portion is in the range of 0.5 cm in width and from 1.0 cm to 2.0 cm in length.

* * * * *